(12) United States Patent
Sluis-Cremer et al.

(10) Patent No.: US 6,811,970 B2
(45) Date of Patent: Nov. 2, 2004

(54) ASSAY FOR IDENTIFYING INHIBITORS OF HIV RT DIMERIZATION

(75) Inventors: Nicolas Sluis-Cremer, Pittsburgh, PA (US); Michael Parniak, Pittsburgh, PA (US); Alex Pelletier, Fabreville (CA)

(73) Assignee: Boehringer Ingelheim (Canada) Ltd., Laval (CA)

(*) Notice: Subject to any disclaimer, the term of this patent is extended or adjusted under 35 U.S.C. 154(b) by 154 days.

(21) Appl. No.: 10/205,641

(22) Filed: Jul. 25, 2002

(65) Prior Publication Data

US 2003/0087379 A1 May 8, 2003

Related U.S. Application Data

(60) Provisional application No. 60/307,883, filed on Jul. 27, 2001.

(51) Int. Cl.$^7$ .................................................. C12Q 1/70
(52) U.S. Cl. .......................... 435/5; 435/6; 435/7.1; 435/7.9; 536/23.72
(58) Field of Search .......................... 435/5, 7.1, 6, 7.9; 536/23.72

(56) References Cited

PUBLICATIONS

Divita, Gilles et al; Dimerization Kinetics of HIV–1 and HIV–2 Reverse Transcriplase: A Two Step Process; J. Mol. Biol. (1995); V. 245; 508–521.
Restle, Tobias et al; Dimerization of Human Immunodeficiency Virus Type 1 Reverse Transcriplase; (1990); The Journal of Biological Chemistry; V. 265; No. 16; 8986–8988.
Restle, Tobias et al; RNase H activity of HIV reverse transcriptases is confined exclusively to the dimeric forms; (1992); FEBS; V. 300; No. 1; 97–100.
Morris, May C. et al; A New Potent HIV–1 Reverse Transcriptase Inhibitor; (1999); The Journal of Biological Chemistry; V. 274; No. 35; 24941–24946.
Cabodevilla, Jesus et al; Factors affecting the dimerazaiton of the p66 of HIV–1 reverse transcriptase; (2001); Eur. of Biochem.; V. 268; 1163–1172.
Divita, Gilles et al; Conformational Stability of Dimeric HIV–1 and HIV–2 Reverse Transcriptases; (1995); *Biochemistry*; V. 34; 16337–16346.
Divita, Gilles et al; *Characterization of the dimerization process of HIV–1 reverse transcriptases* heterodimer using intrinsic protein fluorescence; (1993); FEBS, V. 324; No. 2; 153–158.
Becerra, S. Patricial et al; Protein–Protein Interactions of HIV–1 Reverse Transcriplase: Implication of Central and C–Terminal Regions in Subunit Binding; (1991); Biochemistry; V. 30; 11707–11719.
Tachedjian, Gilda et al; Analysis of mutations and suppressors affecting interactions between the subunits of the HIV type 1 reverse transcriptase; (2000); PNAS; V. 97; No. 12; 6334–6339.
Howard, Kathryn J. et al; Reconstitution and Properties of Homologous and Chimeric HIV–1–HIV2 p66–p51 Reverse Transcriptase; The Journal of Biological Chemistry; (1991); V. 266; No. 34; 23003–23009.
Wong, Jon W. et al; Immobilized Metal Ion Affinity Chromatography (IMAC)—Chemistry and Bioseparation Applications; (1991); Separation and Purification Methods; V. 20; No. 1; 49–106.
Jacobo–Molina, A. et al; HIV Reverse Transciplase Structure–Function Relationships; Biochemistry; 1991; pp. 6351–6361; vol. 30; No. 26.
Arion, Dominique et al; Differences in the Inhibition of Human Immunodeficiency Virus Type 1 Reverse Transcritase DNA Polymerase Activity by Analogs of Nevirapine and [2',5'–bis–o–(Butyldimethylsilyl)–3'–spiro 5'–(4'–amino–1',2'–oxothiole–2',2'–dioxide] (TSAO); Molecular Pharma; 1996; pp. 1057–1064; vol. 50; No. 5.
Tasara, Taurai et al; Intramolecular Chimeras of the p51 Subunit between HIV–1 and FIV Reverse Transcriptases Suggest a Stabilizing Function for the p66 Subunit in the Heterodimeric Enzyme; Biochemistry; 1999; pp. 1633–1642; vol. 38; No. 5.
Morris, May C. et al; The Thumb Domain of the P51–Subunit is the Essential for Activation of HIV Reverse Transcriptase; Biochemistry; 1999; pp. 15097–15103; vol. 38; No. 46.
Tachedijan, Gilda et al; Nonnucleoside reverse transcriptase inhibitors are chemical enhancers of dimerization of the HIV type 1 reverse transcriptase; PNAS; 2001; pp 7188–7193; vol. 98; No. 13.

(List continued on next page.)

Primary Examiner—Jeffrey Stucker
(74) Attorney, Agent, or Firm—Robert P. Raymond; Michael Morris; David A. Dow

(57) ABSTRACT

A method for measuring heterodimerization of HIV RT, which comprises the steps of:
a) providing a first solution comprising p66 subunit homodimers in the presence of a dissociation agent; b) contacting the first solution with p51 RT subunits and incubating in the presence of a reassociation buffer to allow association of a complex of p66/p51 RT subunits, wherein one of the subunits comprises an affinity tag and the other of the subunits comprises a detectable label; c) contacting the incubate of step b) with an affinity medium under conditions that enable the p66/p51 complex to bind to the affinity medium; and d) determining the amount of complex formed by measuring the level of detectable label bound to the affinity medium (or by measuring the reconstituted RT polymerase activity). Steps a) to d) can be carried out in the presence or absence of a test compound followed by e) comparing the test compound sample to a control sample lacking the compound, whereby modulated p66/p51 complex formation in the test compound sample is indicative of the ability of the compound to modulate, inhibit or enhance heterodimerization. The method can be used to screen for inhibitors of HIV RT dimerization.

42 Claims, 4 Drawing Sheets

OTHER PUBLICATIONS

Fletcher, Ronald S. et al; Single–Step Purification of Recombinant Wild–Type and Mutant HIV–1 Reverse Transcriptase; (1996); Protein Expression and Purification; V. 7; No. 0004; 27–32.

Tachedjian, Gilda et al; Nonnucleoside reverse transcriptase inhibitors are chemical enhancers of dimerization of the HIV type 1 reverse transcrilase; (2001); PNAS; V. 98; No. 13; 7188–7193.

Divita, Gilles et al; Inhibition of Human Immunodeficiency Virus Type 1 Reverse Transcriptase Dimerization Using Synthetic Peptides Derived from the Connection Domain; (1994); The Journal of Biological Chemistry; V. 269; No. 18; 13080–13083.

A.

B.

ASSAY FOR IDENTIFYING INHIBITORS OF HIV RT DIMERIZATION

RELATED APPLICATIONS

Benefit of US Provisional Application, Ser. No. U.S. 60/307,883, filed on Jul. 27, 2001, is hereby claimed.

FIELD OF THE INVENTION

The present invention relates to a new assay to measure the process of HIV-1 reverse transcriptase (RT) dimerization. This invention particularly relates to a new method suitable for adaptation to high-throughput screening for inhibitors of this process.

BACKGROUND OF THE INVENTION

Reverse transcriptase (RT) of the human immunodeficiency virus type 1 (HIV-1) plays a key role in the replication of HIV by converting single-stranded genomic RNA into double-stranded proviral DNA and represents one of the main targets for the development of AIDS therapy. Most inhibitors of RT described in the past years, whether nucleoside analogues or non-nucleoside inhibitors target the polymerase activity of RT but present some limitations including toxicity and the emergence of resistant strains.

The biologically relevant and active form of HIV RT found in infectious virions is a heterodimer containing two polypeptides, p66 and p51; the latter derived from the former by proteolytic cleavage of its C-terminal domain during viral maturation. The two subunits of 66 and 51 kDa form are present in a 1 to 1 ratio. This heterodimeric RT is produced in a two-step dimerization process, the kinetics of which involve the rapid association of the two subunits into an immature dimer, followed by a slow conformational change yielding the fully active form (p66+p51→p66/p51 immature→p66/p51 active; Divita et al., 1995, J. Mol. Biol. 245, 508–52112, 13).

The DNA polymerase and RNase H activities of HIV-1 RT are dependent on the dimeric structure of the enzyme (Restle et al., 1990, J. Biol. Chem. 265, 8986–8988; Restle et al., 1992, FEBS Letters 300, 97–100). Because dimerization of these subunits is required for enzymatic activity, interference with the dimerization of HIV-1 RT could constitute an appropriate target for the development of anti-HIV compounds. A case in point: synthetic peptides from the thumb domain of the p51 subunit of RT inhibit the "maturation" process (Morris et al., 1999, Biochemistry 38, 15097–15103). Compounds that interfere with the formation and/or stability of the RT dimer may therefore represent a novel class of antiviral compounds.

Several publications disclose association-dissociation assays for measuring the kinetics of the p51-p66 dimerization process (Cabodevilla et al., 2001, Eur. J. Biochem. 2681163-172; Morris et al., 1999, J.Biol. Chem. 274(35), 2491–24946; Divita et al, 1995, Biochemistry 34, 16337–16346; Divita et al., 1994, J. Biol. Chem. 269(18), 13080–13083; Divita et al., 1993, FEBS Letters 324(2), 153–158; Becerra et al., 1991, Biochemistry 30, 11707–11719). They all proceed to measure the dimerization by either: size-exclusion HPLC; measuring the RNA-dependent DNA polymerase activity of the sample; immunoprecipitation; or by monitoring intrinsic fluorescence emission of the protein. None of these publications disclose a binding assay suitable for HTS format.

Tachedjian et al., 2000 (PNAS 97(12) 6334–6339) disclose a yeast 2-hybrid system to study the association-dissociation process of RT dimerization. However, this system is not easily amenable to a high throughput assay for assessing large numbers of potential inhibitors.

Howard et al., 1991, J. Biol. Chem. 266(34), 23003–23009 suggest an assay system to monitor therapeutic agents that act by preventing dimer formation. Again, this publication does not disclose a binding assay amenable for high throughput screening suitable for the identification of potential inhibitors of heterodimerization.

SUMMARY OF THE INVENTION

The present invention provides a high-throughput assay suitable for assessing large numbers of compounds for their activity against the dimerization of HIV RT. The general principle of the assay of the present invention involves dissociating a p66/p66 RT homodimer (appropriately labeled with a detectable moiety and/or affinity tagged) in the presence of limiting concentrations of a dissociation agent (i.e. a denaturant such as urea), contacting it with the p51 RT subunit and incubating the mixture in the presence of an excess denaturant-free (or denaturant reduced) buffer to allow re-association of the RT subunits, with subsequent affinity capture of any reconstituted p51/p66 RT heterodimer.

After washing to remove unbound material, the amount of affinity-associated material is assessed by measuring the level of a detectable moiety (or alternatively, by measuring the reconstituted RT polymerase activity in which case the p66 subunit does not necessarily require labeling), and is proportional to the amount of labeled p66/p51 RT heterodimer bound by affinity. This assay is performed in the presence or absence of a test compound whereby a modulation (decrease/increase) in binding of p66 monomer subunit to p51 subunit in the presence of the test compound compared to the control is indicative that the test compound is a modulator of RT dimerization.

In a first aspect of the present invention, there is provided a method for measuring heterodimerization of HIV RT, which comprises the steps of:
 a) providing a first solution comprising p66 subunit homodimers in the presence of a dissociation agent;
 b) contacting said first solution with p51 RT subunits and incubating in the presence of a reassociation buffer to allow association of a complex of p66/p51 RT subunits, wherein one of said subunits comprises an affinity tag and the other of said subunits comprises a detectable label;
 c) contacting the incubate of step b) with an affinity medium under conditions that enable the p66/p51 complex to bind to said affinity medium; and
 d) determining the amount of complex formed by measuring the level of detectable label bound to the affinity medium (or by measuring the reconstituted RT polymerase activity).

In a second aspect of the present invention, there is provided a method for identifying compounds capable of modulating the HIV RT heterodimerization, comprising:
 carrying out steps a) to d) described above in the presence or absence of a test compound; and
 e) comparing the test compound sample to a control sample lacking said compound, whereby modulated p66/p51 complex formation in the test compound sample is indicative of the ability of said compound to modulate heterodimerization.

In a third aspect of the present invention, there is provided a method for identifying compounds capable of interfering with the HIV RT heterodimerization, comprising:

carrying out steps a) to d) described above in the presence or absence of a test compound; and e) comparing the test compound sample to a control sample lacking said compound, whereby decreased p66/p51 complex formation in the test compound sample is indicative of the ability of said compound to inhibit heterodimerization.

In a fourth aspect of the present invention, there is provided a method for identifying compounds capable of enhancing the HIV RT heterodimerization, comprising:

carrying out steps a) to d) described above in the presence or absence of a test compound; and e) comparing the test compound sample to a control sample lacking said compound, whereby increased p66/p51 complex formation in the test compound sample is indicative of the ability of said compound to enhance heterodimerization.

According to a fifth aspect of the present invention, there is provided a method for measuring homodimerization of HIV RT, which comprises the steps of:

a) providing a first solution comprising first p66 subunit homodimers in the presence of a dissociation agent;

b) contacting said first solution with second p66 subunits homodimers, in the presence of said dissociation agent, and incubating in the presence of a reassociation buffer to allow association of a complex of p66/p66 RT subunits, wherein one of said subunits comprises an affinity tag and the other of said subunits comprises a detectable label;

c) contacting the incubate of step b) with an affinity medium under conditions that enable the p66/p66 complex to bind to said affinity medium; and d) determining the amount of complex formed by measuring the level of detectable label bound to the affinity medium (or by measuring the reconstituted RT polymerase activity).

In a sixth aspect of the present invention, there is provided a method for identifying compounds capable of modulating the HIV RT homodimerization, comprising:

carrying out steps a) to d) described above in the presence or absence of a test compound; and e) comparing the test compound sample to a control sample lacking said compound, whereby modulated p66/p66 complex formation in the test compound sample is indicative of the ability of said compound to modulate homodimerization.

In a seventh aspect of the present invention, there is provided a method for identifying compounds capable of interfering with the HIV RT homodimerization, comprising:

carrying out steps a) to d) described above in the presence or absence of a test compound; and e) comparing the test compound sample to a control sample lacking said compound, whereby decreased p66/p66 complex formation in the test compound sample is indicative of the ability of said compound to inhibit homodimerization.

In a eighth aspect of the present invention, there is provided a method for identifying compounds capable of enhancing the HIV RT homodimerization, comprising:

carrying out steps a) to d) described above in the presence or absence of a test compound; and e) comparing the test compound sample to a control sample lacking said compound, whereby increased p66/p66 complex formation in the test compound sample is indicative of the ability of said compound to enhance homodimerization.

According to a ninth aspect of the present invention, there is provided a kit for testing compounds potentially modulating the HIV RT heterodimerization, said kit comprising a plurality of affinity-tagged p66 subunit homodimers, a plurality of labeled-p51 RT subunits, a dissociation agent, a reassociation buffer, an affinity medium and instructions on how to use said subunits for identifying test compounds binding to said transcriptase.

According to a tenth aspect of the present invention, there is provided a kit for testing compounds potentially modulating the HIV RT homodimerization, said kit comprising a plurality of affinity-tagged p66 subunit homodimers, a plurality of labeled-p66 RT subunits, a dissociation agent, a reassociation buffer, an affinity medium and optionally instructions on how to use said subunits for identifying test compounds binding to said transcriptase.

Other objects, advantages and features of the present invention will become more apparent upon reading of the following non-restrictive description of the preferred embodiments with reference to the accompanying drawings which is exemplary and should not be interpreted as limiting the scope of the invention.

BRIEF DESCRIPTION OF THE DRAWINGS

Having thus generally described the invention, reference will now be made to the accompanying drawings, showing by way of illustration a preferred embodiment thereof, and in which.

DETAILED DESCRIPTION OF THE PREFERRED EMBODIMENTS

Definitions

Figure 1:
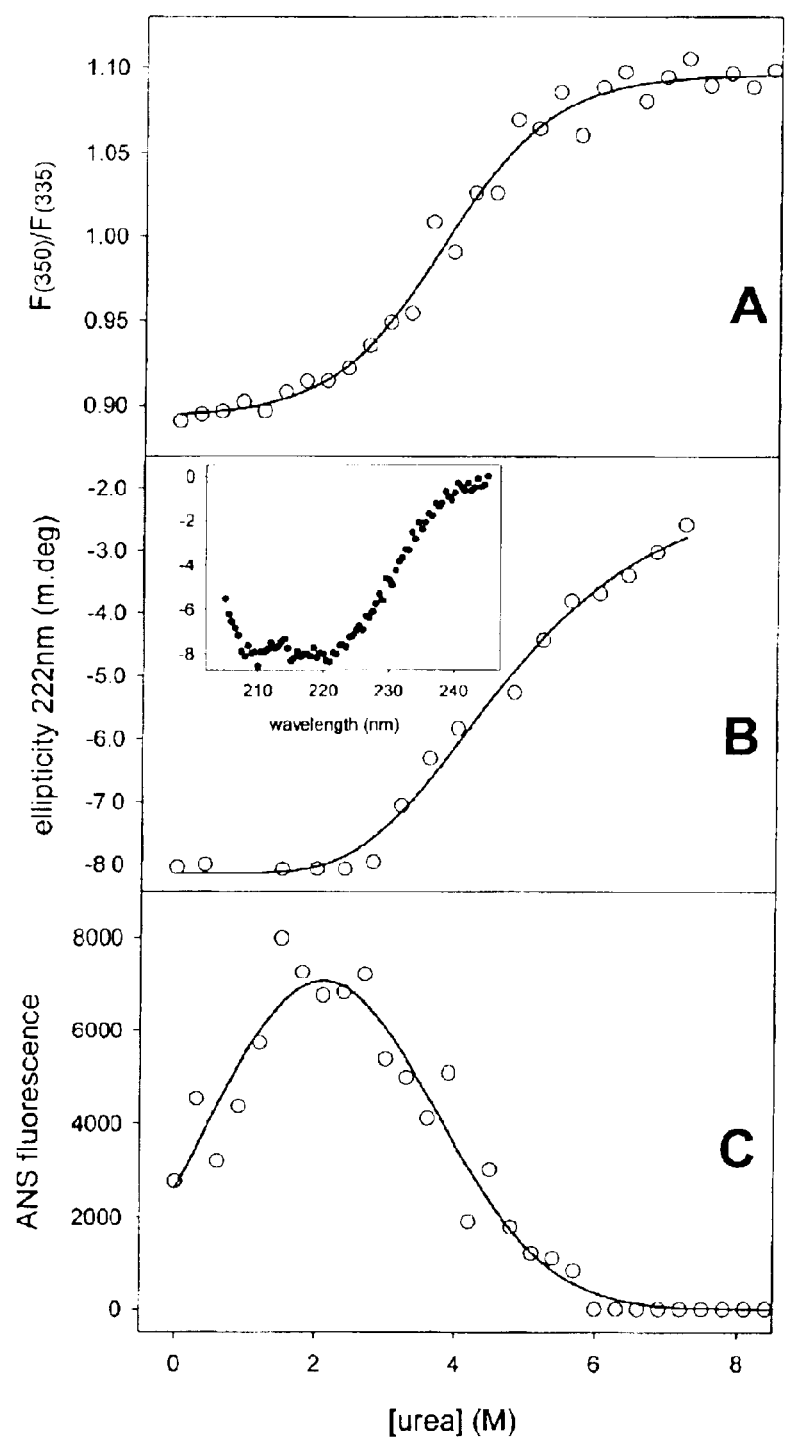
FIG. 1 illustrates the effect of urea concentration on HIV-1 p66/p66 RT protein structure. Panel A illustrates the change in intrinsic protein fluorescence emission maximum wavelength as a function of urea concentration. The increase in the F350/335 ratio indicates an increased exposure of normally 'buried' tryptophan residues to aqueous solvent. Panel B illustrates results of circular dichroism analyses. The increase in molar ellipticity at 222 nm is a measure of the loss of RT secondary structure. Panel C shows the change in 8-anilino-1-naphthalene-sulfonic acid (ANS) binding to RT, which correlates with the subunit integrity of the RT dimer.

Unless otherwise defined, all technical and scientific terms used herein have the same meaning as those commonly understood by one of ordinary skill in the art to which the invention pertains.

As used herein, the terms "label", detectable label" or "detectable marker" refer to any group that may be linked to the p66 or p51 to allow recognition either directly or indirectly of the subunit such that it can be detected, measured and quantified. Examples of such "labels" include, but are not limited to, fluorescent labels, chemiluminescent labels, colorimetric labels, enzymatic markers, radioactive isotopes and affinity tags such as biotin. Such labels are attached to the p66 or p51 by well known methods. A label, or multiple labels, of the present invention can be introduced at any position on the p66 or the p51, for example, the label can be at either the C- or N-termini or within the main chain of the protein.

The term "affinity label" or "affinity tag" as used herein refers to a label, which is specifically trapped by a complementary affinity ligand. Examples of pairs of affinity tag/affinity ligand include but are not limited to: Maltose-Binding Protein (MBP)/maltose; Glutathione S Transferase (GST)/glutathione; streptavidin tag/streptavidin or neutravidin, or histidine (His)/metal. The metal used as affinity ligand may be selected from the group consisting of: cobalt, zinc, copper, iron, and nickel (Wong et al. (1991) Separation and Purification Methods, 20(1), 49–106). The affinity tag of the present invention can be introduced at any position on the p66 or the p51, for example, the tag can be at either the C- or N-termini or within the main chain of the protein, but preferably on the N-terminus of the protein. Preferably, the metal selected is nickel. The affinity ligand can be set up in solid phase such as: beads, microplate wells or columns to facilitate separation by affinity chromatography. Such affinity tags may be introduced recombinantly to p66 or p51 by well-known methods.

The terms "monomer" and "monomeric" p66 or "monomeric" subunit refer to a single subunit of a dimeric p66. The monomeric subunit may be an exact copy of the naturally occurring monomeric subunit or it may be either a biologically active analog or a biologically inactive analog (negative dominant).

As used herein, the term "subunit", when referring to either p66 or p51, is intended to mean one or two constituents of homodimeric RT (p66/p66) or heterodimeric RT (p66/p5).

As used herein, the term "homodimer" refers to a dimeric molecule wherein both subunits are the same, for example p66/p66.

As used herein, the term "homodimerization" refers to the process by which same subunits, namely p66, dimerize.

As used herein, the term "heterodimer" refers to a dimeric molecule wherein the two subunit constituents are different, for example p66 and p51.

As used herein, the term "heterodimerization" refers to the process by which two different subunits, namely p66 and p51, dimerize.

As used herein, the term "dissociation agent" refers to a substance that is capable of dissociating a multicomponent complex into its individual subunits.

As used herein, the term "reassociation buffer" refers to a buffer that favors association of the individual subunits into a multicomponent complex.

As used herein, the term "denaturant free" refers to conditions in which the dissociation agent is no longer present in quantities sufficient to prevent association of the majority of subunits.

As used herein, the term "affinity medium" is intended to mean a solid support such as microplate wells, beads, or column which are coated with an affinity ligand that is suitable to capture an affinity tag.

Preferred Embodiments

In a first preferred aspect of the first embodiment, there is provided a method for measuring heterodimerization of HIV RT, wherein preferably, the first solution in step a) comprises a buffer selected from Tris-HCl, HEPES or bis-Tris. More preferably, the buffer is Tris-HCl at a concentration of between 0 mM and 50 mM. Most preferably, the buffer is Tris-HCl at a concentration of 25 mM.

Preferably, the first solution in step a) further comprises a salt selected from $Na_2SO_4$ or $MgCl_2$. More preferably, the salt is $MgCl_2$ at a concentration of between 0 mM and 100 mM.

In a preferred aspect of the first embodiment in step a), the dissociation agent is selected from urea, guanidinium-HCl or acetonitrile. More preferably, the dissociation agent is urea at a concentration from 1 to 3.5 M.

Preferably, the re-association buffer in step b) is the same buffer used to dissociate the p66/p66 subunits but is preferably denaturant-free. More preferably, the re-association buffer is present in excess amount to the denaturant buffer to dilute the dissociation agent sufficiently to allow re-association of p66 and p51 subunits. Most preferably, the re-association buffer is added in a 10-fold excess over the dissociation buffer.

Preferably, the re-association buffer in step b) further comprises a salt selected from $Na_2SO_4$ or $MgCl_2$. More preferably, the salt is $Na_2SO_4$ at a concentration of between 0 mM and 100 mM. Most preferably, the salt is $Na_2SO_4$ at a concentration of 50 mM.

Preferably, the p51 in step b) is affinity-tagged or has a detectable label. More preferably, the p51 in step b) is affinity-tagged.

Preferably, the p66 in step b) has a detectable label or is affinity-tagged. More preferably, the p66 in step b) has a detectable label.

Preferably, the affinity-tag in step b) is selected from the group consisting of: a hexa-histidine tag, FLAG, T7, HA, GST, or biotin. More preferably, the affinity tag is hexa-histidine.

In another preferred aspect if the first embodiment in step b), the detectable label is selected from the group consisting of: a fluorescent label (such as fluorescein, Oregon green, rhodamine, Texas-red, phycoerythrin or $Eu^{3+}$), a radioactive atom (such as $^3H$ or $^{125}I$), a chemiluminescent label (such as luciferase), a detectable antibody specific to p66 or specific to a tag attached to p66 (preferably, the tag on p66 is selected from the group consisting of: a hexa-histidine tag, FLAG, T7, HA, GST, or biotin), and an enzymatic marker (such as β-galactosidase or horseradish peroxidase). More preferably, the label is a fluorescent label selected from the group consisting of: fluorescein, Oregon green, rhodamine, Texas-red, phycoerythrin and $Eu^{3+}$). Most preferably, the fluorescent label is $Eu^{3+}$.

Preferably, the detectable label in step b) is added to a cysteine residue that is introduced recombinantly in place of a proline residue at the N-terminus of p66.

The detectable label is measured by appropriate means such as fluorometer, radioactivity counter, colorimeter or chemiluminometer as will be readily recognized by a person of skill in the art.

In another preferred aspect of the first embodiment in step c), the affinity medium is a solid phase such as microplate wells or beads coated with an affinity-ligand that is suitable to capture the affinity tag. More preferably, the microplate wells are coated with a receptor selected from the group consisting of: $Ni^{2+}$, anti-tag antibodies, glutathione or streptavidin. Most preferably, the microplate wells are coated with $Ni^{2+}$, and preferably the affinity tag is a histidine tag. A person skilled in the art will recognize the suitable combinations of affinity-tag and affinity-ligand.

In a preferred aspect of the first embodiment, step d) further comprises the step of washing to remove unbound material, the amount of affinity medium-associated label being measured in an appropriate fashion (or the polymerase activity of the reconstituted RT being measured), wherein material bound to said affinity medium is proportional to the amount of labeled p51/p66 RT heterodimer.

As will be readily recognized by persons skilled in the art, the sequence of events in the assay leading to the incubation of p66 monomer and p51 can be modified with the same outcome. For example: the p51 RT subunit can be immobilized to a solid-phase prior to its incubation with p66 subunit. Similarly, the dilution of buffer promoting subunit association can take place at the same time as mixing of the p66 and p51 subunits or after the p66 solution has been contacted with p51.

Similarly, the contacting of the test compound can be carried out in a different sequence without affecting the principle of the assay. For example, the test compound can be added to the p66 homodimer solution prior to addition of the dissociation agent; prior to the mixing with the p51 subunit; prior to the dilution with the re-association buffer; or at the same time as dilution with the re-association buffer.

EXAMPLES

Materials and Methods

1. RT Expression Plasmids

The gene for the 51 kDa subunit of HIV-1 RT (HXB2 strain) was cloned into the pBAD HisB prokaryotic expression system (Invitrogen) between the XhoI and HindIII restriction sites, to give pBAD-HisRT51. This construct allows for the arabinose-inducible expression of the p51 subunit of RT as an N-terminal polyhistidine (6xHis) fusion protein following transformation of an appropriate bacterial strain (e.g., E. coli JM109).

To provide for specific labeling of the 66 kDa RT subunit with reagents allowing fluorometric detection, site-directed mutagenesis was carried out using Quick Change™ Site-directed Mutagenesis Kit (Stratagene) to produce P2C/C38S/C280S RT. This eliminated the two Cys residues of WT (Wild Type) RT (C38, C280) and inserted a single Cys residue near the N-terminus of the subunit.

The genes for the WT and the P2C/C38S/C280S (SEQ ID NO. 1) 66 kDa subunit of HIV-1 RT were cloned into the pKK223-3 prokaryotic expression vector (Amersham Pharmacia Biotech) between the Eco R1 and Hind III restriction sites, to yield pKK-RT66WT and pKK-RT66-P2C, respectively. These vectors provide for the IPTG-dependent expression of the non-HIS-tagged 66 kDa RT subunit.

2. Reagents for TRF Assay of RT Dimer Formation

Delfia Eu-N1-iodoacetomido chelate and $Eu^{3+}$ Standard, Delfia Enhancement solution and Delfia wash concentrate were purchased from Perkin Elmer.

Ultrapure urea, tris(hydroxymethyl)aminomethane and water were acquired from Fluka. Magnesium chloride (SigmaUltra) and diethylenetriamine-pentaacetic acid (DTPA) were from Sigma.

96-well Ni-NTA HisSorb plates (white) were purchased from Qiagen or Pierce. Fluorescence measurements were made with a SpectraMAX GeminiXS microplate fluorometer (Molecular Devices).

3. Expression and Purification of RT p51 Subunit Monomer and the RT p66/p66 Homodimer E. coli JM109 transformed with pBAD-HisRT51 were grown at 37° C. in "Terrific broth" to mid-log phase ($OD_{600}$ of 0.5). Expression of p51 RT was then induced by the addition of 1% arabinose. After further incubation for 3 h, cells were harvested by centrifugation and lysed using BugBuster™ protein extraction reagent (Novagen). The p51 RT was purified from the lysate by $Ni^{2+}$-NTA affinity chromatography, using His-Bind Resin (Novagen). Both lysis and extraction were carried out according to the manufacturer's specifications. Following elution from $Ni^{2+}$-NTA resin, p51 RT was buffer-exchanged into 50 mM Tris-HCl (pH 7.5, 4° C.) containing 60 mM $MgCl_2$ and 50% glycerol, by two passages through NAP™25 column (Amersham Pharmacia Biotech). The final protein sample was stored in aliquots at −80° C. Purified p51 RT exists predominantly as a monomer.

Expression of WT and mutant p66 RT was induced by the addition of 1 mM IPTG to 1 L of appropriately transformed mid-log phase E. coli JM109 cells (grown in "Terrific broth" at 37° C.). Following addition of IPTG, growth of the bacteria was continued at 32° C. for an additional 5 hours. Cells were harvested by centrifugation. Purification of the p66 RT was carried out as previously described (Fletcher et al., 1996, "Single step purification of HIV-1 recombinant wild type and mutant reverse transcriptase" *Protein Expression & Purification* 7, 27–32). Purified p66 RT exists predominantly as a homodimer.

4. Alkylation of P2C/C38S/C280S p66/p66 RT with the $Eu^{3+}$-N1-Iodoacetamido Chelate Purified P2C/C38S/C280S p66/p66 RT was concentrated to approximately 20 μM (~2.5 mg/ml) in 50 mM Tris-HCl buffer (pH 7.9 at 20° C.) containing 100 mM NaCl and 1 mM TCEP-HCl (Tris(2-carboxyethyl)phosphine hydrochloride (Pierce)) at room temperature. An aliquot of Eu-N1-iodoacetamido chelate protein-modification reagent (prepared as a 5 mM stock solution in DMSO) was added to provide an approximately 20-fold molar excess relative to the p66 subunit concentration. The alkylation reaction was allowed to proceed for up to 6 hours at room temperature. Alternatively, the reaction may be carried out overnight at 4° C. Upon completion of the reaction, an excess of DTT was added to consume unreacted Eu-N 1-iodoacetamido chelate. The alkylated p66/p66 RT was separated from the DTT-reagent conjugate by two passages through a NAPT™ 25 column equilibrated with a 25 mM Tris-HCl buffer (pH 7.5, 20° C.) containing 60 mM $MgCl_2$ and 50% glycerol. The stoichiometry of labeling was generally found to be between 0.7-1 mol of Eu-N1-iodoacetamide per mol of p66 RT subunit (i.e., 1.5–2 mol/mol p66/p66 RT homodimer).

Kinetic characterization of the mutant and the chemically modified RT proteins indicated that the P2C/C38S/C280S p66/p66 RT possessed comparable RNA-dependent DNA polymerase (RDDP) specific activity to the wt p66/p66 homodimer enzyme (data not shown). The P2C/C38S/C280S p66/p66 RT chemically alkylated with the Eu-N1-iodoacetamido chelate retains approximately 80% of the RDDP activity of the unmodified protein (Table 1). In addition, the modified RT is equally sensitive to inhibition by TSAO$e^3$T (Table 2) as the unmodified P2C/C38S/C280S p66/p66 mutant, which in turn is equally sensitive as WT p66/p66 RT (data not shown). Thus, the genetic and chemical manipulations of RT required to prepare reagents for the dimerization assay appear to have little effect on the response of the enzyme within the parameters of the assay protocol.

TABLE 1

RNA-dependent DNA polymerase (RDDP) and DNA-dependent DNA polymerase (DDDP) specific activity of P2C/C38S/C280S p66/p66 RT.

| Polymerase substrate | % activity relative to unlabeled p66/p66 Eu$^{3+}$-labeled p66/p66 |
|---|---|
| Poly rC:dG | 80 |
| Poly rA:dT | 77 |
| Poly dC:dG | 73 |

TABLE 2

Inhibition of P2C/C38S/C280S p66/p66 RT by HIV RT inhibitors.

| | IC$_{50}$ ($\mu$M) | |
|---|---|---|
| Inhibitor | unlabeled p66/p66 | Eu$^{3+}$-labeled p66/p66 |
| Nevirapine | 1 | 1 |
| TSAOe3T | 3 | 3 |

5. Microplate Assay to Monitor p66-p51 RT Dimerization

The general principle of the assay involves mixing of His6x-p51 with fluorophore-labeled p66 RT in solution, with subsequent solid-phase capture of resulting His6x-p51/fluorophore-labeled p66 RT heterodimer on Ni$^{2+}$-NTA microplates. After washing to remove unbound material, the amount of microplate-associated fluorescence is measured in an appropriate fluorescence plate reader. Alternatively, the polymerase activity of the reconstituted RT can be determined by using a fluorescent RNA/DNA intercalator such as PicoGreen™.

While purified recombinant p51 RT exists as a monomer, purified p66 RT is predominantly dimeric. Since the subunit association energy of the p66/p66 RT homodimer is only minimally less than that of the p51/p66 RT heterodimer, the formation of the heterodimer following simple mixing of p51 and p66/p66 RT would be too slow to be convenient in a high throughput assay. Accordingly, a search was carried out to determine the optimal type and concentration of denaturant needed to provide dissociation of the p66/p66 homodimer without significant effect on protein secondary structure. Urea was found to be superior to guanidinium chloride as denaturant. The effect of urea concentration on p66/p66 dissociation and over protein denaturation (change in protein secondary structure) is shown in FIG. 1. Optimization of the urea concentration for maximization of the TRF signal in the dimerization assay system is given in FIG. 3.

Figure 2:
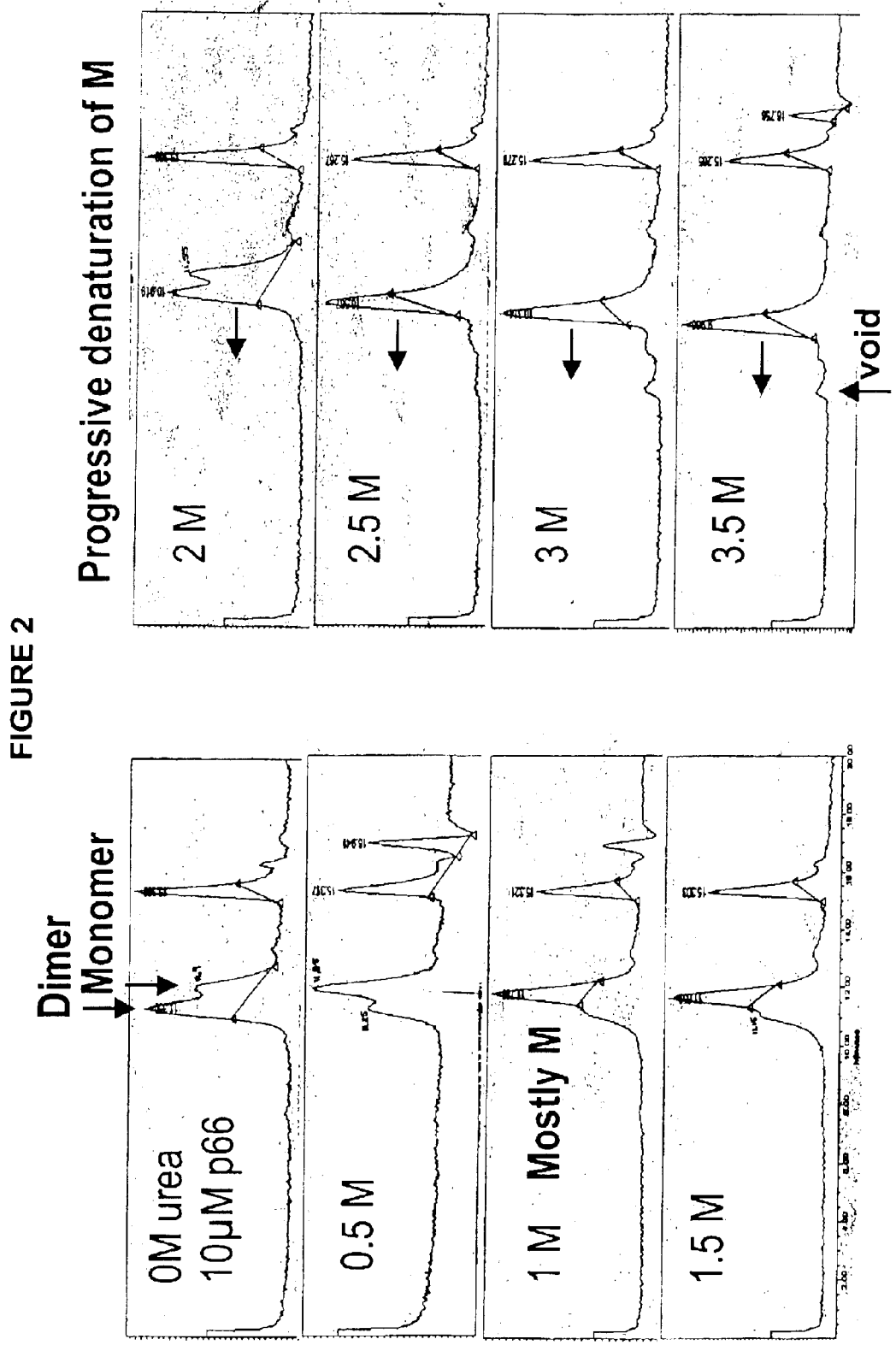
FIG. 2 illustrates the dimerization state of p66 subunit as a function of urea concentration as determined by size-exclusion chromatography.
Figure 3:
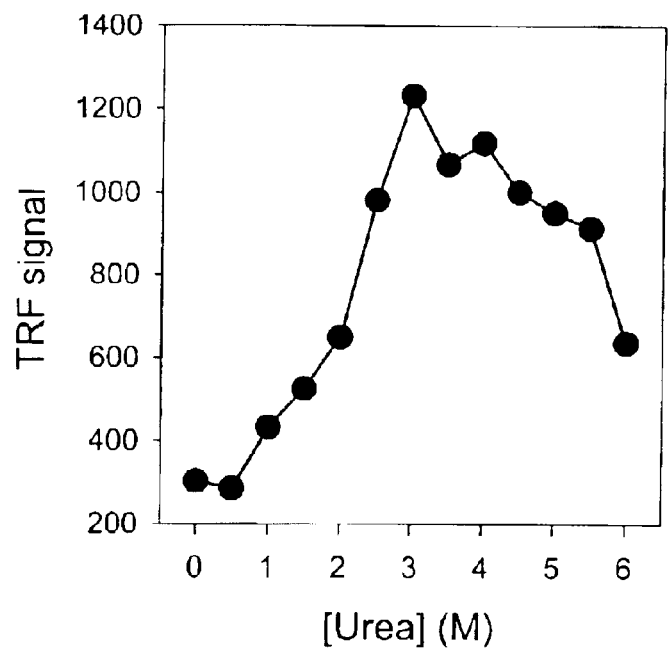
FIG. 3 illustrates the optimization of urea concentration for use in the TRF (Time Resolved Fluorescence) assay for HIV-1 RT p66/p51 heterodimer formation.
Figure 4:
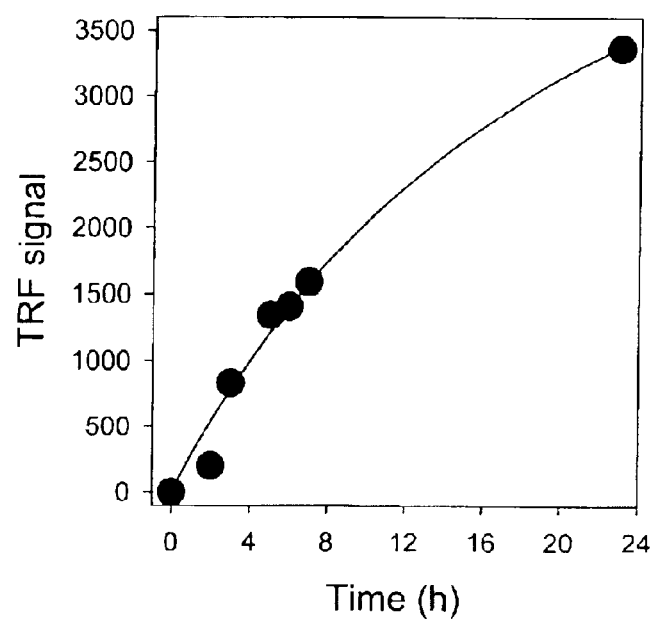
FIG. 4 illustrates the specific TRF signal as a function of time following dilution of urea-denatured His6x-p51 RT subunit and Eu-N1-iodoacetamido chelate labeled p66 RT subunit into "subunit association" buffer containing 100 mM $MgCl_2$. Details are described in the examples.

Urea at 1–3.5M was found to be optimal, based on a variety of data, including those illustrated in FIGS. 1, 2 and 3. There are a large number of tryptophan residues at the subunit interface of HIV-1 RT; these are essentially "buried" and therefore fluoresce at about 335 nm when RT is excited at wavelengths between 280–295 nm. As can be seen in FIG. 1A, these residues become increasingly "solvent exposed" with increasing urea concentrations, as indicated by the red-shift in $\lambda_{max}^{em}$ to 350 nm. At 3.5M urea, this red-shift is approximately half-maximal. At the same time, however, this concentration of urea has little effect on the molar ellipticity of RT (FIG. 1B), indicating that the protein secondary structure may not be significantly altered (i.e., no significant "denaturation" of the protein has occurred). This suggests that the increased solvent exposure of the protein tryptophan residues arises primarily from dissociation of the RT subunits. The changes in ANS binding to RT as a function of urea concentration (FIG. 1C) are consistent with this interpretation.

FIG. 2 shows the change in the dimerization state of p66/p66 RT as a function of urea as determined by size-exclusion chromatography. In this case, dissociation of the homodimer appears essentially complete at 2M urea and a progressive denaturation/aggregation of the p66 monomer appears to take place as the peak slowly shifts toward higher molecular weights with increasing urea concentrations. FIG. 3 shows the signal obtained in the time-resolved RT subunit reassociation assay when labeled RT p66/p66 homodimer and His-tagged p51 monomer were incubated in urea concentrations between 0–6 M, prior to addition of the mixture to the Nickel-coated microplates. Thus, 1–3.5M urea was selected as the concentration range likely to provide the highest level of re-association with the least detrimental effect on RT secondary structure.

Additional experiments show that the use of 50 mM Na$_2$SO$_4$ rather than 100 mM MgCl$_2$ in the renaturation buffer significantly enhances the TRF specific signal to background in the assay (Table 3).

TABLE 3

Signal to noise ratio in the RT dimerization assay as a function of renaturation buffer salt composition.

| Label on p66 RT | Salt | S/N |
|---|---|---|
| Tetramethyl rhodamine | 100 mM MgCl$_2$ | 2.0 |
| Oregon Green | 100 mM MgCl$_2$ | 3.2 |
| Eu-N1-iodoacetamide (TRF) | 100 mM MgCl$_2$ | 6.5 |
| Eu-N1-iodoacetamido (TRF) | 50 mM Na$_2$SO$_4$ | 10.8 |

6. Antiviral Activity of RT Subunit Disrupters and RT Subunit Association Inhibitors.

Assay Protocol

Figure 5:
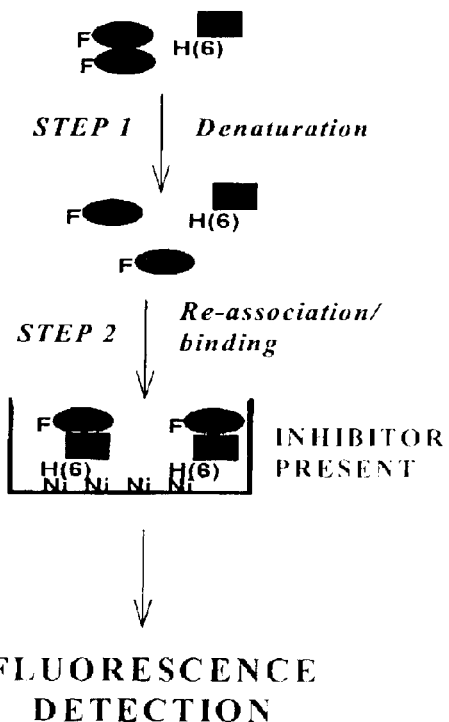
FIG. 5 illustrates the assay concept (Panel A) and Inhibition of HIV-1 RT dimerization by TSAO-$m^3$T and other NNRTIs (Panel B), as measured by TRF.
Figure 5:
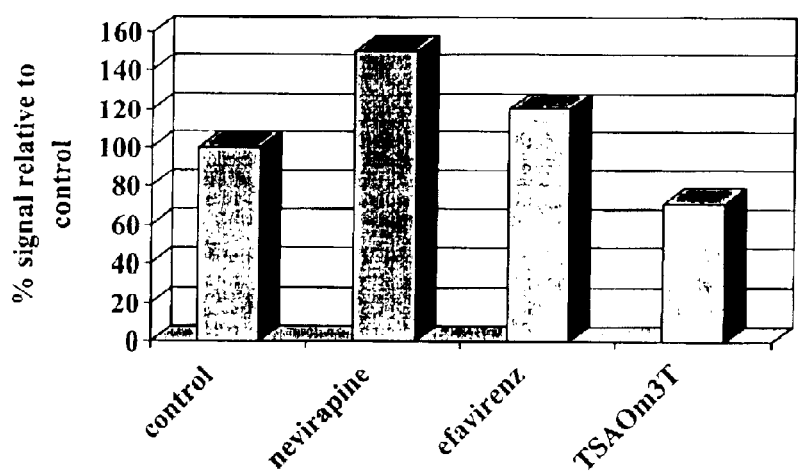

The concept of the assay is shown in FIG. 5A. In a total volume of 20 $\mu$l, mix 100 pmol of purified His6x-p51 RT subunit and 200 pmol of Eu-N1-iodoacetamido chelate labeled p66 RT subunit (i.e., 100 pmol RT p66/p66 homodimer) with urea (prepared in 25 mM Tris-HCl pH 7.5, 20° C., containing 100 mM MgCl$_2$) to provide a final concentration of 3.5 M urea. Incubate this mixture for 1 h at room temperature.

Dilute this solution into 200 $\mu$L of a solution of the compound of interest at 10 $\mu$M (in 25 mM Tris-HCl pH 7.5, 20° C., containing 50 mM Na$_2$SO$_4$) contained in a well of a 96-well Ni-NTA HiSorb Plate.

The dilution step provides a 10-fold dilution to reduce the urea concentration from 3.5M to 0.35M, thereby allowing formation of the RT p66/p51 heterodimer. Dimer formation is allowed to proceed for 6 h, then the plates are washed 3× with Delfia wash buffer containing 200 $\mu$M DTPA. After washing, 200 $\mu$L of the Delfia enhancement solution is added to each well, followed by incubation at room temperature for 30 minutes. Fluorescence measurements are made using a Molecular Devices SpectraMAX GeminiXS instrument, using excitation, emission and cutoff wavelengths of 335 nm, 615 nm and 530 nm, respectively. Using this format, TSAOm$^3$T decreases the signal in the assay of the invention (FIG. 5B). TSAOm$^3$T is part of the TSAO family and is thought to inhibit RT dimerization to a similar degree as TSAOe$^3$T. In addition, nevirapine and efavirenz are two non-nucleoside reverse transcriptase inhibitors that do not inhibit the enzyme via RT dimerization. In fact, it has been reported that these two NNRT inhibitors are chemical enhancers of dimerization of the HIV-1 RT causing inhibition of the polymerase activity through deleterious conformational changes (Tachedjian et al., 2001, PNAS, 7188–7193). In this particular assay format, the % signal relative to control presented in FIG. 5B is supportive of this hypothesis and supports the usefulness of the present assay to identify inhibitors/enhancers of the HIV RT dimerization process.

Alternatively, the polymerase activity of the reconstituted p66/p51 reverse transcriptase can be measured. In this format, the necessary substrates (template primer, nucleotide, magnesium chloride) in an appropriate buffer (Tris pH 7.8 containing DTT, GSH & Chaps) are added directly to the wells following the dimerization step and incubated for 1 hour after which time the amount of polymerization is determined by addition of a fluorescent RNA/DNA intercalator. An example is as follows: The homodimer p66/p66 (10–20 pmols) is incubated in the presence of HIS-p51 (25-50 pmols) in 1 M urea (prepared in 20 mM Tris-HCl pH 8.0 containing 250 mM NaCl) in a final volume of 10 μL for 1 hour to allow dissociation of the homodimer. Then an initial 5-fold dilution (final volume of 50 μL) in re-association buffer (50 mM Tris-acetate, pH 8.0, 500 mM NaCl, 0.05% Tween-20, 0.01% BSA) with a test compound in the association buffer, is performed for 1–2 hours to allow for heterodimer formation by reduction of the urea concentration to 200 mM. The final step consists of capturing the reconstituted His-tagged heterodimers by transferring the sample in the wells of a nickel plate containing 100 μL of re-association buffer and incubating for 1 hour. After 3 washing cycles, a polymerase assay cocktail is added and the reaction is allowed to proceed for 1–2 hours at 37° C. before the elongated RNA/DNA products are detected with the fluorescent intercalator PicoGreen™.

7. Alternative Format of the Assay

The biologically relevant and active form of HIV RT found in infectious virions is a heterodimer containing two polypeptides, p66 and p51; the latter derived from the former by proteolytic cleavage of its C-terminal domain by HIV protease during viral maturation. The two subunits of 66 and 51 kDa form are present in a 1 to 1 ratio. This heterodimeric RT is believed to be produced in a two-step dimerization process, the kinetics of which involve the rapid association of the p66 and p51 subunits into an immature dimer, followed by a slow conformational change yielding the fully active form (p66+p51→p66/p51 immature→p66/p51 active; Divita et al., 1995, J. Mol. Biol. 245, 508–52112, 13).

However, more recent evidence has also suggested an alternate mechanism for the formation of RT which first involves homodimerization of the p66 subunits into a p66/p66 homodimer followed by HIV protease cleavage into a p66/p51 heterodimer (Oral presentation, Retrovirus 2001 Cold Spring Harbor, N.Y., May 26, 2001). It is unclear at this time which mechanism prevails during viral replication and screening assays designed to probe each pathway individually may offer new therapeutic approaches. It is therefore another aspect of this invention to probe for compounds that can potentially interfere with the homodimerization of p66 subunits.

What is claimed is:

1. A method for measuring heterodimerization of HIV RT, which comprises the steps of:
   a) providing a first solution comprising p66 subunit homodimers in the presence of a dissociation agent;
   b) contacting said first solution with p51 RT subunits and incubating in the presence of a reassociation buffer to allow association of a reconstituted RT complex of p66/p51 RT subunits, wherein one of said subunits comprises an affinity tag and the other of said subunits comprises a detectable label;
   c) contacting the incubate of step b) with an affinity medium under conditions that enable the p66/p51 complex to bind to said affinity medium; and
   d) determining the amount of complex formed by measuring the level of detectable label bound to the affinity medium.

2. The method according to claim 1, wherein in step d), said amount of complex is determined by measuring the polymerase activity of said reconstituted RT complex.

3. The method, according to claim 1, wherein the first solution in step a) comprises a buffer selected from the group consisting of Tris-HCl, HEPES and bis-Tris.

4. The method, according to claim 2, wherein the buffer is Tris-HCl at a concentration of between 0mM and 50mM.

5. The method, according to claim 1, wherein the first solution in step a) further comprises a salt selected from Na2SO4 or MgCl2.

6. The method, according to claim 5, wherein the salt is MgCl2 at a concentration of between 0mM and 100 mM.

7. The method, according to claim 1, wherein in step a), the dissociation agent is selected from the group consisting of urea, guanidinium-HCl and acetonitrile.

8. The method, according to claim 7, wherein the dissociation agent is urea at a concentration from 1 to 3.5 M.

9. The method, according to claim 1, wherein the re-association buffer in step b) is the same buffer used to dissociate the p66/p66 subunits, said re-association buffer being denaturant-free.

10. The method, according to claim 1, wherein the re-association buffer is present in excess amount to the denaturant buffer to dilute the dissociation agent sufficiently to allow re-association of p66 and p51 subunits.

11. The method, according to claim 10, wherein the re-association buffer is added in a 10-fold excess over the dissociation buffer.

12. The method, according to claim 1, wherein the re-association buffer in step b) further comprises a salt selected from Na2SO4 or MgCl12.

13. The method, according to claim 12, wherein the salt is Na2SO4 at a concentration of between 0 mM and 100 mM.

14. The method, according to claim 13, wherein the salt is Na2SO4 at a concentration of 50 mM.

15. The method, according to claim 1, wherein the p51 in step b) is affinity-tagged or has a detectable label.

16. The method, according to claim 15, wherein the p51 in step b) is affinity-tagged.

17. The method, according to claim 1, wherein the p66 in step b) has a detectable label or is affinity-tagged.

18. The method, according to claim 17, wherein the p66 in step b) has a detectable label.

19. The method, according to claims 15, wherein the affinity-tag in step b) is selected from the group consisting of: a hexa-histidine tag, FLAG, T7, HA, GST, and biotin.

20. The method, according to claim 1, wherein the affinity-tag in step b) is selected from the group consisting of: hexa-histidine tag, FLAG, T7, HA, GST, and biotin.

21. The method, according to claim 19, wherein the affinity tag is hexa-histidine.

22. The method, according to claims 15, wherein the detectable label is selected from the group consisting of: a fluorescent label, a radioactive atom, a chemiluminescent label, a detectable antibody specific to p66 or specific to a tag attached to p66, and an enzymatic marker.

23. The method, according to claim 17, wherein the detectable label is selected from the group consisting of: a fluorescent label, a radioactive atom, a chemiluminescent label, a detectable antibody specific to p66 or specific to a tag attached to p66, and an enzymatic marker.

24. The method, according to claim 21, wherein the detectable label is a fluorescent label selected from the group consisting of: fluorescein, Oregon green, rhodamine, Texas-red, phycoerythrin and $Eu^{3+}$.

25. The method, according to claim 22, wherein the fluorescent label is Eu3+.

26. The method, according to claim 1, wherein the detectable label in step b) is added to a cysteine residue that is introduced recombinantly in place of a proline residue at the N-terminus of p66.

27. The method, according to claim 1, wherein the affinity medium in step c) captures any reconstituted labeled-p66/tag-p51/RT heterodimer.

28. The method, according to claim 1, wherein in step c), the affinity medium is a solid phase coated with a receptor that is suitable to capture the affinity tag.

29. The method, according to claim 26, wherein the solid phase is coated with a receptor selected from the group consisting of: $Ni^{2+}$, anti-tag antibodies, glutathione and streptavidin.

30. The method, according to claim 27, wherein solid phase is coated with $Ni^{2+}$.

31. The method, according to claim 26, wherein the affinity tag is histidine.

32. The method, according to claim 26, wherein the solid phase is a microplate.

33. The method, according to claim 1, wherein step d) further comprises the step of washing to remove unbound material, the amount of affinity medium-associated label being measured or the polymerase activity of the reconstituted RT being measured, wherein material bound to said affinity medium is proportional to the amount of labeled p51/p66 RT heterodimer.

34. A method for identifying compounds capable of modulating the HIV RT heterodimerization, comprising:
   carrying out steps a) to d), according to claim 1, in the presence or absence of a test compound; and
   e) comparing the test compound sample to a control sample lacking said compound, whereby modulated p66/p51 complex formation in the test compound sample is indicative of the ability of said compound to modulate heterodimerization.

35. A method for identifying compounds capable of interfering with the HIV RT heterodimerization, comprising:
   a) providing a first solution comprising p66 subunit homodimers in the presence of a dissociation agent;
   b) contacting said first solution with p51 RT subunits and incubating in the presence of a reassociation buffer to allow association of a reconstituted RT complex of p66/p51 RT subunits, wherein one of said subunits comprises an affinity tag and the other of said subunits comprises a detectable label;
   c) contacting the incubate of step b) with an affinity medium under conditions that enable the p66/p51 complex to bind to said affinity medium; and d) determining the amount of complex formed by measuring the level of detectable label bound to the affinity medium, wherein steps a) to d), are performed in the presence or absence of a test compound; and e) comparing the test compound sample to a control sample lacking said compound, whereby decreased p66/p51 complex formation in the test compound sample is indicative of the ability of said compound to inhibit heterodimerization.

36. A method for identifying compounds capable of enhancing the HIV RT heterodimerization, comprising:

carrying out steps a) to d), according to claim 1, in the presence or absence of a test compound; and e) comparing the test compound sample to a control sample lacking said compound, whereby increased p66/p51 complex formation in the test compound sample is indicative of the ability of said compound to enhance heterodimerization.

37. A method for measuring homodimerization of HIV RT, which comprises the steps of:

a) providing a first solution comprising first p66 subunit homodimers in the presence of a dissociation agent;

b) contacting said first solution with second p66 subunits homodimers, in the presence of said dissociation agent, and incubating in the presence of a reassociation buffer to allow association of a complex of p66/p66 RT subunits, wherein one of said subunits comprises an affinity tag and the other of said subunits comprises a detectable label;

c) contacting the incubate of step b) with an affinity medium under conditions that enable the p66/p66 complex to bind to said affinity medium; and d) determining the amount of complex formed by measuring the level of detectable label bound to the affinity medium or by measuring the reconstituted RT polymerase activity.

38. A method for identifying compounds capable of modulating the HIV RT homodimerization, comprising:

carrying out steps a) to d), according to claim 37, in the presence or absence of a test compound; and e) comparing the test compound sample to a control sample lacking said compound, whereby modulated p66/p66 complex formation in the test compound sample is indicative of the ability of said compound to modulate homodimerization.

39. A method for identifying compounds capable of interfering with the HIV RT homodimerization, comprising:

carrying out steps a) to d), according to claim 37, in the presence or absence of a test compound; and e) comparing the test compound sample to a control sample lacking said compound, whereby decreased p66/p66 complex formation in the test compound sample is indicative of the ability of said compound to inhibit homodimerization.

40. A method for identifying compounds capable of enhancing the HIV RT homodimerization, comprising:

carrying out steps a) to d), according to claim 37, in the presence or absence of a test compound; and e) comparing the test compound sample to a control sample lacking said compound, whereby increased p66/p66 complex formation in the test compound sample is indicative of the ability of said compound to enhance homodimerization.

41. A kit for testing compounds potentially modulating the HIV RT heterodimerization, said kit comprising a plurality of affinity-tagged p66 subunit homodimers, a plurality of labeled p51 RT subunits, a dissociation agent, a reassociation buffer, and an affinity medium.

42. A kit for testing compounds potentially modulating the HIV RT homodimerization, said kit comprising a plurality of affinity tagged p66 subunit homodimers, a plurality of labeled p66 RT subunits, a dissociation agent, a reassociation buffer, and an affinity medium.

* * * * *

SEQUENCE LISTING

<160> NUMBER OF SEQ ID NOS: 1

<210> SEQ ID NO 1
<211> LENGTH: 560
<212> TYPE: PRT
<213> ORGANISM: HXB2 HIV-1 P66C2P

<400> SEQUENCE: 1

```
Cys Ile Ser Pro Ile Glu Thr Val Pro Val Lys Leu Lys Pro Gly Met
 1               5                  10                  15

Asp Gly Pro Lys Val Lys Gln Trp Pro Leu Thr Glu Glu Lys Ile Lys
            20                  25                  30

Ala Leu Val Glu Ile Ser Thr Glu Met Glu Lys Glu Gly Lys Ile Ser
        35                  40                  45

Lys Ile Gly Pro Glu Asn Pro Tyr Asn Thr Pro Val Phe Ala Ile Lys
    50                  55                  60

Lys Lys Asp Ser Thr Lys Trp Arg Lys Leu Val Asp Phe Arg Glu Leu
65                  70                  75                  80

Asn Lys Arg Thr Gln Asp Phe Trp Glu Val Gln Leu Gly Ile Pro His
                85                  90                  95

Pro Ala Gly Leu Lys Lys Lys Lys Ser Val Thr Val Leu Asp Val Gly
            100                 105                 110

Asp Ala Tyr Phe Ser Val Pro Leu Asp Glu Asp Phe Arg Lys Tyr Thr
        115                 120                 125

Ala Phe Thr Ile Pro Ser Ile Asn Asn Glu Thr Pro Gly Ile Arg Tyr
    130                 135                 140

Gln Tyr Asn Val Leu Pro Gln Gly Trp Lys Gly Ser Pro Ala Ile Phe
145                 150                 155                 160
```

-continued

Gln Ser Ser Met Thr Lys Ile Leu Glu Pro Phe Arg Lys Gln Asn Pro
                165                 170                 175

Asp Ile Val Ile Tyr Gln Tyr Met Asp Asp Leu Tyr Val Gly Ser Asp
                180                 185                 190

Leu Glu Ile Gly Gln His Arg Thr Lys Ile Glu Leu Arg Gln His
            195                 200                 205

Leu Leu Arg Trp Gly Leu Thr Thr Pro Asp Lys Lys His Gln Lys Glu
            210                 215                 220

Pro Pro Phe Leu Trp Met Gly Tyr Glu Leu His Pro Asp Lys Trp Thr
225                 230                 235                 240

Val Gln Pro Ile Val Leu Pro Glu Lys Asp Ser Trp Thr Val Asn Asp
                245                 250                 255

Ile Gln Lys Leu Val Gly Lys Leu Asn Trp Ala Ser Gln Ile Tyr Pro
                260                 265                 270

Gly Ile Lys Val Arg Gln Leu Ser Lys Leu Leu Arg Gly Thr Lys Ala
                275                 280                 285

Leu Thr Glu Val Ile Pro Leu Thr Glu Glu Ala Glu Leu Glu Leu Ala
            290                 295                 300

Glu Asn Arg Glu Ile Leu Lys Glu Pro Val His Gly Val Tyr Tyr Asp
305                 310                 315                 320

Pro Ser Lys Asp Leu Ile Ala Glu Ile Gln Lys Gln Gly Gln Gly Gln
                325                 330                 335

Trp Thr Tyr Gln Ile Tyr Gln Glu Pro Phe Lys Asn Leu Lys Thr Gly
                340                 345                 350

Lys Tyr Ala Arg Met Arg Gly Ala His Thr Asn Asp Val Lys Gln Leu
            355                 360                 365

Thr Glu Ala Val Gln Lys Ile Thr Thr Glu Ser Ile Val Ile Trp Gly
            370                 375                 380

Lys Thr Pro Lys Phe Lys Leu Pro Ile Gln Lys Glu Thr Trp Glu Thr
385                 390                 395                 400

Trp Trp Thr Glu Tyr Trp Gln Ala Thr Trp Ile Pro Glu Trp Glu Phe
                405                 410                 415

Val Asn Thr Pro Pro Leu Val Lys Leu Trp Tyr Gln Leu Glu Lys Glu
                420                 425                 430

Pro Ile Val Gly Ala Glu Thr Phe Tyr Val Asp Gly Ala Ala Asn Arg
            435                 440                 445

Glu Thr Lys Leu Gly Lys Ala Gly Tyr Val Thr Asn Arg Gly Arg Gln
450                 455                 460

Lys Val Val Thr Leu Thr Asp Thr Thr Asn Gln Lys Thr Glu Leu Gln
465                 470                 475                 480

Ala Ile Tyr Leu Ala Leu Gln Asp Ser Gly Leu Glu Val Asn Ile Val
                485                 490                 495

Thr Asp Ser Gln Tyr Ala Leu Gly Ile Ile Gln Ala Gln Pro Asp Gln
            500                 505                 510

Ser Glu Ser Glu Leu Val Asn Gln Ile Ile Glu Gln Leu Ile Lys Lys
            515                 520                 525

Glu Lys Val Tyr Leu Ala Trp Val Pro Ala His Lys Gly Ile Gly Gly
        530                 535                 540

Asn Glu Gln Val Asp Lys Leu Val Ser Ala Gly Ile Arg Lys Val Leu
545                 550                 555                 560